United States Patent [19]

Dee et al.

[11] 4,377,641

[45] Mar. 22, 1983

[54] METHOD AND APPARATUS FOR THE CONTINUOUS EXTRACTION OF INGREDIENTS FROM SAMPLES

[75] Inventors: Louis A. Dee, Quartz Hill; Mary E. Fiske, Lancaster, both of Calif.

[73] Assignee: The United States of America as represented by the Secretary of the Air Force, Washington, D.C.

[21] Appl. No.: 313,859

[22] Filed: Oct. 22, 1981

[51] Int. Cl.³ .......................................... G01N 31/06
[52] U.S. Cl. .............................. 436/178; 73/61.1 C; 210/198.3; 210/658; 422/70; 436/162; 436/20; 436/21; 436/126
[58] Field of Search ............... 23/230 R; 422/69, 70; 73/61.1 C; 210/198.3, 658

[56] References Cited

U.S. PATENT DOCUMENTS

| | | | |
|---|---|---|---|
| 3,327,857 | 6/1967 | Kopp | 210/658 |
| 4,028,060 | 6/1977 | Godsey | 23/293 R |
| 4,065,384 | 12/1977 | Pandey et al. | 210/658 |
| 4,313,906 | 2/1982 | Filipi | 73/61.1 C |

FOREIGN PATENT DOCUMENTS 1321861  2/1963  France .............................. 210/198.3

OTHER PUBLICATIONS

J. A. Barnard et al., *Modern Methods of Chemical Analysis*, (1969) pp. 189-218.
H. A. Flaschka et al., *Quantitative Analytical Chemistry*, vol. 1, *Introduction to Principle*, (1969) pp. 517-519.

*Primary Examiner*—Michael S. Marcus
*Attorney, Agent, or Firm*—Donald J. Singer; John R. Flanagan

[57] ABSTRACT

A method and apparatus for continuous extraction of an ingredient from a sample employs a container having a solvent therein selected for its ability to extract the ingredient. The sample is held against a porous substrate having a lower portion which is located below the sample and placed in the solvent, and an upper portion which is located above the sample and exposed to a selected atmosphere. In a continuous supply from the container, solvent is caused to ascend the substrate by capillary action, penetrate the sample, extract the ingredient therefrom, and continue to ascend the upper portion of the substrate where it evaporates, depositing the extracted ingredient thereon. The upper portion of the substrate containing the ingredient may then be removed.

6 Claims, 2 Drawing Figures

METHOD AND APPARATUS FOR THE CONTINUOUS EXTRACTION OF INGREDIENTS FROM SAMPLES

RIGHTS OF THE GOVERNMENT

The invention described herein may be manufactured and used by or for the Government of the United States for all governmental purposes without the payment of any royalty.

BACKGROUND OF THE INVENTION

1. Field of the Invention

The present invention broadly relates to solvent extraction procedures and, more particularly, is concerned with a method and apparatus for quantitatively separating and isolating major to ultratrace levels of extractable ingredients in small quantity samples of various materials.

2. Description of the Prior Art

Solvent extraction is regularly carried out in laboratories by chemists as a conventional procedure in analytical separations wherein the extraordinary ability of certain solvents to quantitatively and preferentially remove one or more constituents or ingredients from a solution or solid material sample is exploited.

One type of laboratory apparatus for extracting organic materials from a sample of a solid matrix containing such organic materials is described and illustrated in U.S. Pat. No. 4,028,060 to Godsey. Through a repeated sequence of alternately heating and cooling opposite ends of the apparatus, the solvent is made to repeatedly pass through the sample until the solvent passing also through the permeable sample support is substantially clear indicating that substantially all of the organic material has been removed from the sample.

However, the apparatus of the aforesaid patent has several drawbacks. First, it takes technical skill to perform the steps of the procedure. Second, applications for the apparatus are limited in scope. Third, the apparatus requires auxiliary equipment, such as cooling and heating sources. Fourth, use of the apparatus with a solvent presents an explosion hazard since it is necessary to heat a portion of the sealed apparatus to approximately 100° C. above the solvent boiling point. Fifth, the solvent containing the extract must be heated to 100° C. above the solvent boiling point; therefore, reactive extracts are likely to decompose during the extraction process. Sixth, sequential solvent extraction is impossible on a single sample unless the sample is removed and reassembled in a second apparatus. Finally, the extraction solvent containing the extract must be quantitatively transferred from the tubular member and the solvent evaporated prior to gravimetric analysis.

Therefore, a need exists for a simple, inexpensive and versatile procedure for separating and extracting a wide variety of chemical mixtures for quantitative and qualitative analysis or identification.

SUMMARY OF THE INVENTION

The present invention provides a continuous extraction method and apparatus designed to satisfy the aforementioned needs. In addition, the invention provides automatic concentration of the extracted ingredient and control of the size of the surface upon which the ingredient is located. This avoids the frequently encountered problem in some prior art procedures of needing to accumulate large volumes of dilute solutions of the extracted ingredient in order to extract all of the ingredient from the sample. Thus, the technique herein presented provides for continuous liquid extraction of even diminishing small quantities of an ingredient without the accumulation of increasing dilute solutions thereof. Also, in the present invention, the solvent containing the extracted constituent is never recycled through the sample. Therefore, the solvent will not end up contaminating the sample as the extraction process proceeds to completion.

Accordingly, the present invention provides a method and apparatus for continuous extraction of a selected ingredient from a sample containing the same. The extraction method and apparatus employs a container having a solvent therein which is selected for its ability to extract the ingredient from the sample. Also, a porous substrate to be placed into the solvent in the container is utilized. The porous substrate has a lower portion for placement into the solvent to cause the solvent to ascend the substrate by capillary action. Additionally, the porous substrate has a middle portion in contact with the lower substrate portion and disposed above the level of the solvent for engaging the sample to allow the solvent to penetrate the sample and extract the ingredient therefrom. Finally, the porous substrate has an upper portion in contact with and extending above the middle substrate portion and substantially exposed to a selected atmosphere for allowing the solvent and extracted ingredient carried therewith to ascend the upper substrate portion from the sample. Also, the solvent is allowed to evaporate from the upper substrate portion and deposit the extracted ingredient thereon. Holding means holds the sample against the middle portion of the substrate so as to substantially inhibit evaporation of the solvent from the substrate at the location of the sample.

More particularly, the porous substrate includes a pair of first and second porous strips each defining the lower and middle portions of the substrate, and a third porous strip separate from the first and second strips and defining the upper portion of the substrate. The holding means includes a pair of nonporous plates for clamping the sample and lower end of the third porous strip between upper ends of the first and second porous strips. The third strip at its lower end is disposed above the sample and between the upper ends of the first and second strips so as to extend therefrom above the plates for exposure to the atmosphere and facilitate ease of removal from contact with the first and second strips and replacement by another similar strip.

DETAILED DESCRIPTION OF THE INVENTION

Figure 1:
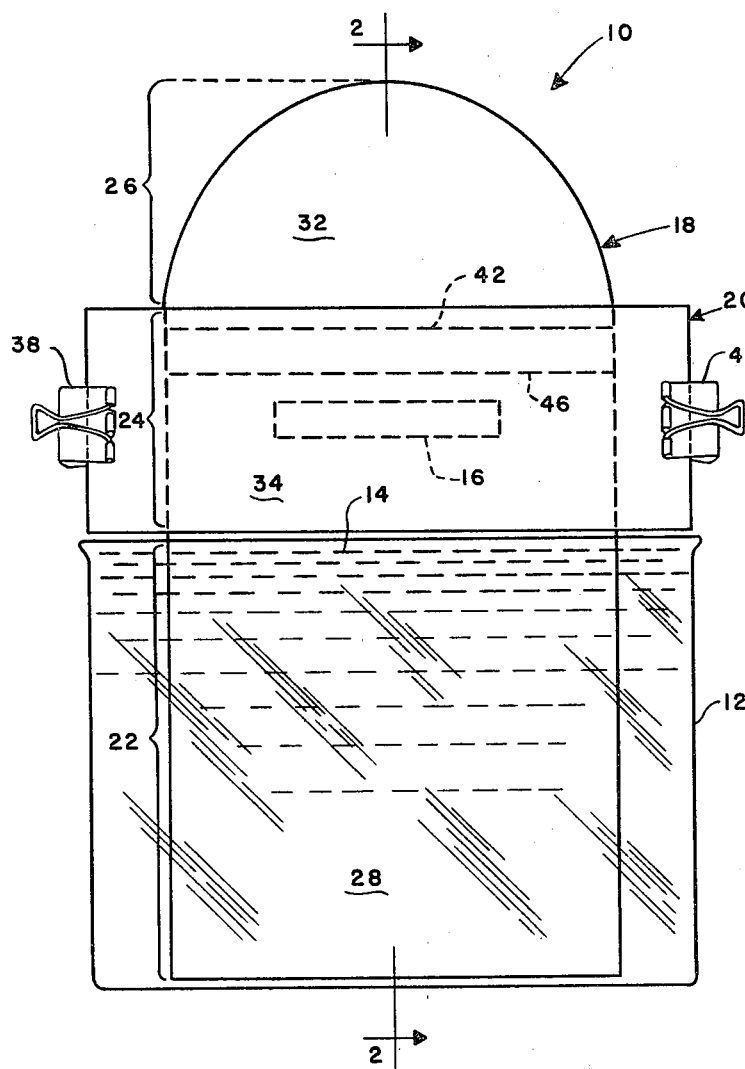
FIG. 1 is a front elevational view of the continuous extraction apparatus of the present invention.
Figure 2:
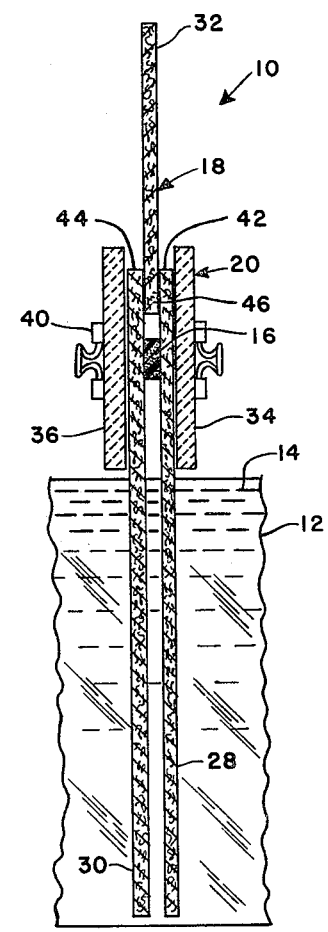
FIG. 2 is a cross-sectional view taken along line 2—2 of FIG. 1.

Referring now to the drawings, there is shown the preferred embodiment of the continuous extraction apparatus of the present invention, being generally designated 10. The apparatus 10 includes a container 12 having a quantity of a suitable solvent 14 therein. A solvent is selected which has the ability to extract a particular desired ingredient from a sample 16 undergoing investigation.

The apparatus 10 also includes a porous substrate, generally designated 18, and means 20 for holding the sample 16 against the substrate 18. A lower portion 22 (FIG. 1) of the substrate 18 is placed in the solvent 14. A middle portion 24 (FIG. 1) of the substrate is retained by the holding means 20 against the sample 16. An upper portion 26 (FIG. 1) of the substrate 18 is exposed to a selected atmosphere. Both the middle and upper portions 24, 26 of the substrate 18 are disposed above the level of the solvent 14 in the container 12.

In the preferred embodiment of the apparatus 10, the porous substrate 18 is comprised by three parts: a pair of substantially identical first and second porous strips 28 and 30; and a third porous strip 32. The first and second strips 28, 30 each define the lower and middle portions 22, 24 of the substrate 18, while the third strip 32 defines the upper portion 26 thereof. The holding means 20 includes a pair of moderately rigid, nonporous plates 34, 36 disposed along opposite sides of the middle portion 26 of the substrate 18 and clamping the same therebetween by a pair of releasable clamps 38, 40 engaging opposite ends of the plates. Specifically, upper ends 42, 44 of the first and second strips 30, 32, respectively, are disposed between the plates 34, 36 with the sample 16 and the lower end 46 of the third strip 32 in contact with and disposed between the first and second strip upper ends 42, 44. The plates 34, 36 thereby substantially shield the sample 16 and the upper ends 42, 44 of first and second strips 28, 30 from the atmosphere which inhibits evaporation of solvent from the substrate 18 at the location of the sample 16. The lower end 46 of the third strip 32 is disposed above the sample 16, while the remainder of the third strip 32 extends therefrom above the plates for exposure to the atmosphere. Preferably, the upper ends 42, 44 of the first and second strips 28, 30 extend beyond all sides of the sample 16.

When the lower portion 22 of the substrate 18 is placed into the solvent 14 in the container 12, as seen in the drawings, capillary action causes the solvent to rise up or ascend the porous strips 28, 30 to the location of the sample 16. The solvent 14 then penetrates the sample and extracts therefrom the particular ingredient of interest. The solvent, now containing the ingredient, continues to ascend the substrate 10, in particular, rising up to the third strip 32 to the portion thereof extending above the clamping plates 34, 36 where the third strip is exposed to the selected atmosphere. Evaporation of the solvent from this portion of the third strip 32 deposits the extracted ingredient on the exposed portion of the third strip and causes a continuous supply of fresh solvent from the container 12 to ascend the substrate, penetrate the sample, extract the ingredient therefrom, and deposit additional quantities of the extracted ingredient on the upper portion 26 of the substrate. The upper portion of the substrate, or more specifically the third strip 32, can then be removed and subjected to further analysis.

In such manner, selective and successive extractions can be accomplished on the same sample simply by replacement of the third strip and immersion of the lower portion of the substrate into the next solvent. Alternatively, numerous extractions of different samples can be effected simultaneously by placing a number of substrates carrying different samples into the same solvent reservoir or container. There are no size limitations on the apparatus. The dimensions of the apparatus are dictated by the size of the sample to be subjected to the extraction process. Furthermore, the shape and size of the removable porous third strip 32 may be varied to concentrate the extracted ingredient in a small area thereof or disperse it over a large area. Normally, in one to two hours, the extractable ingredient will be quantitatively located on the third strip 32. The removable strip containing the extracted ingredient can then be removed, dried, weighed, or subjected to further solvent extraction for subsequent analysis as desired. Also, the apparatus can be used for quantitative determination of sensitive ingredients, such as nitroglycerine.

A more complete understanding of the present invention can be obtained by referring to the following illustrative examples of the practice of the invention, which examples are not intended, however, to be unduly limitative of the invention. On the contrary, the examples demonstrate the potential for practice of the invention in a variety of applications.

EXAMPLE I

A thin strip of a sample of solid porpellant (1.5"×0.25"×0.005", 0.25 g) which contained 0.95% Di-n-octyl phthalate was placed between two strips of Whatman No. 1 filter paper (2"×4"). Also a removable semicircle strip (0.75" dia.) of Whatman No. 1 paper was placed between the other two strips near the propellant sample. Two glass plates (1.0"×3.0"×0.1") were clamped over the propellant sample and the bottom portion of the semicircle strip. The 2×4 strips of filter paper extending below the glass plates were placed in a vessel containing low residue dichloromethane and allowed to stand for two hours in a dry nitrogen atmosphere at ambient temperature. The semicircle strip of filter paper was removed and the upper portion which visibly indicated the presence of an extract was cut off and placed in a vial containing five milliliters of 1, 2-dichloroethane. This mixture was allowed to stand for approximately ten minutes with occasional shaking. A portion of the solution was then transferred to an 0.1 mm pathlength sealed liquid infrared cell and the absorbance of the 1287 $cm^{-1}$ peak was determined. This absorbance when compared to calibration standards appropriate correction for dilution indicated that the sample contained 0.98% di-n-octylphthalate. A recovery of 103% is shown.

EXAMPLE II

A thin section of skin from a sample of fresh orange (1"×0.25"×0.004") was treated in a manner similar to the sample of Example I except that diethyl ether was used as the extraction solvent. A small portion of the ether extract of the semicircle strip (0.5 ml) was evaporated on a KCl plate and the infrared spectrum of the residue matched that of organe oil. The extracted skin was dry and very brittle indicating that the only remaining substances were cellular or pulp.

EXAMPLE III

A thin section of a sample of uncooked ham (1"×0.25"×0.003") was treated in a manner similar to the sample of Example I except that diethyl ether was used as the extraction solvent. A small portion of the ether extract of the semicircle strip (0.5 ml) was evaporated on a KCl plate and the infrared spectrum of the residue matched that of a fatty acid ester. The extracted sample was very dry and brittle indicating that no fat or moisture remained.

EXAMPLE IV

Approximately 0.5 milligram samples of scrapings from a wooden bench, a painted fabric, and a small lipstick smear on paper were treated in a manner similar to the sample of Example I except that the extraction solvent was benzene. A small portion (0.5 ml) of the benzene extracts of the semicircle paper strips were evaporated on KCl plates and the subsequent infrared spectra were readily identified as an alkyd resin from the wooden bench, a vinyl acetate resin from the fabric paint, and a polyglycol/fatty acid ester mixture from the lipstick smear.

EXAMPLE V

A thin section of a sample of solid propellant of unknown oxidizer content (0.25"×1.5"×0.003", 0.1 gram) was extracted with dichloromethane as in Example I except that the extract was collected on a semicircular tared filter paper strip. After one hour another tared paper strip was inserted in its place. The extraction substrate with the new tared paper strip was then placed in a 70/30 volume percent acetone/water solution and allowed to stand for two hours. This tared paper strip was then removed and both were dried at 40° for one hour and reweighed. The resulting weight increases of the paper semicircle strips showed that the solid propellant contained 8% dichloromethane extractable material and 70% acetone/water extractable material which is typical of many solid propellant formulations.

Summarizing, Example I demonstrates the quantitative accuracy of the present invention. Examples II and III, on the other hand, demonstrate the applicability of the invention for recovery of materials from plant or animal tissues for subsequent analysis for such things as pesticides, vitamins, lipid composition, etc. Example IV demonstrates the applicability of the invention for identification of very small samples associated with forensic science. Finally, Example V demonstrates the use of the device for multiple solvent extraction on the same sample.

It is thought that the continuous solvent extraction method and apparatus of the present invention and many of its attendant advantages will be understood from the foregoing description and it will be apparent that various changes may be made in the steps and parts thereof without departing from the spirit and scope of the invention or sacrificing all of its material advantages, the form hereinbefore described being merely a preferred or exemplary embodiment thereof.

Having thus described the invention, what is claimed is:

1. A method of extracting an ingredient from a sample, comprising the steps of:
   (a) holding a sample containing the ingredient to be extracted between and in contact with upper ends of a pair of first and second porous strips with a third porous strip at its lower end being inserted between and in contact with said upper ends of said first and second strips above the position of said sample therebetween;
   (b) placing lower ends of said first and second strips located below said sample into a container of solvent to cause said solvent to ascend said first and second strips by capillary action, penetrate said sample, extract said ingredient therefrom, and continue to ascend said third strip toward its upper end located above said sample and carry said extracted ingredient therewith;
   (c) evaporating said solvent from said upper end of said third strip to deposit said extracted ingredient thereon; and
   (d) removing said third strip with said ingredient deposited thereon.

2. The extracting method as recited in claim 1, wherein said evaporating of said solvent from said upper end of said third strip causes a continuous supply of fresh solvent from said container to ascend said first and second strips, penetrate said sample, extract said ingredient therefrom and deposit additional quantities of said extracted ingredient on said upper end of said third strip.

3. The extracting method as recited in claim 1, wherein said sample is held against said first and second strips so as to substantially inhibit evaporation of said solvent therefrom at the location of said sample.

4. Apparatus for extracting an ingredient from a sample, comprising:
   (a) a container;
   (b) a solvent within said container being selected for its ability to extract said ingredient from said sample;
   (c) a pair of first and second porous strips having respective lower ends for placement into said solvent in said container to cause said solvent to ascend said first and second strip by capillary action and respective upper ends disposed above the level of said solvent for engaging said sample to allow said solvent to penetrate said sample and extract said ingredient therefrom;
   (d) a third strip at its lower end being inserted between, in contact with and extending above said upper ends of said first and second strips and substantially exposed to a selected atmosphere for allowing said solvent and extracted ingredient carried therewith to ascend said third strip from said sample toward the upper end of said third strip and said solvent to evaporate from said upper end of said third strip and deposit said extracted ingredient thereon; and
   (e) means for holding said sample between and in contact with said upper ends of said first and second strips so as to substantially inhibit evaporation of said solvent from said first and second strips at the location of said sample.

5. The extracting apparatus as recited in claim 1, wherein said holding means includes a pair of nonporous plates for clamping said sample and said lower end of said third porous strip between upper ends of said first and second porous strips.

6. The extracting apparatus as recited in claim 1, wherein said third porous strip is selectively removable from contact with said first and second strips for replacement by a substantially similar strip.

* * * * *